United States Patent
Tsuji et al.

[11] Patent Number: 5,861,952
[45] Date of Patent: Jan. 19, 1999

[54] OPTICAL INSPECTION METHOD AND APPARATUS INCLUDING INTENSITY MODULATION OF A LIGHT BEAM AND DETECTION OF LIGHT SCATTERED AT AN INSPECTION POSITION

[75] Inventors: Toshihiko Tsuji, Atsugi; Kyoichi Miyazaki, Mitaka; Seiji Takeuchi, Kawasaki; Minoru Yoshii, Tokyo; Noriyuki Nose, Atsugi, all of Japan

[73] Assignee: Canon Kabushiki Kaisha, Tokyo, Japan

[21] Appl. No.: 984,509

[22] Filed: Dec. 2, 1992

[30] Foreign Application Priority Data

Nov. 16, 1992 [JP] Japan ................. 4-305423

[51] Int. Cl.$^6$ ................. G01B 9/02; G01N 21/88
[52] U.S. Cl. ................. 356/349; 356/237
[58] Field of Search ................. 356/237, 349

[56] References Cited

U.S. PATENT DOCUMENTS

| | | | |
|---|---|---|---|
| 4,030,830 | 6/1977 | Holly | 356/237 X |
| 4,669,875 | 6/1987 | Shiba et al. | 356/237 |
| 4,842,408 | 6/1989 | Yoshii et al. | 356/349 |
| 5,022,757 | 6/1991 | Modell | 356/349 X |
| 5,028,797 | 7/1991 | Abe et al. | 250/548 |
| 5,030,842 | 7/1991 | Koshinaka et al. | 250/571 |
| 5,148,037 | 9/1992 | Suda et al. | 250/548 |

*Primary Examiner*—Vincent P. McGraw
*Attorney, Agent, or Firm*—Fitzpatrick, Cella, Harper & Scinto

[57] ABSTRACT

A light source portion having an acousto-optic element produces a laser beam of two light components having a frequency difference $\Delta w$ and having registered polarization directions. The laser beam is subsequently divided by a half mirror. One of the divided laser beams is detected by a photoelectric detector as reference light, and a corresponding signal is applied to a synchronism detector. The other laser beam is projected by a scanning optical system to the surface of, e.g., an original to be examined to scan the same. At the position on the surface irradiated by the scanning light spot, the laser beam is modulated at a beat frequency $\Delta w$ on the basis of optical heterodyne interference. A synchronism detector detects a signal corresponding to the scattered light from a particle or defect on the surface being examined, in synchronism with the frequency of the reference light, whereby the particle or defect can be detected with a good signal-to-noise ratio.

8 Claims, 8 Drawing Sheets

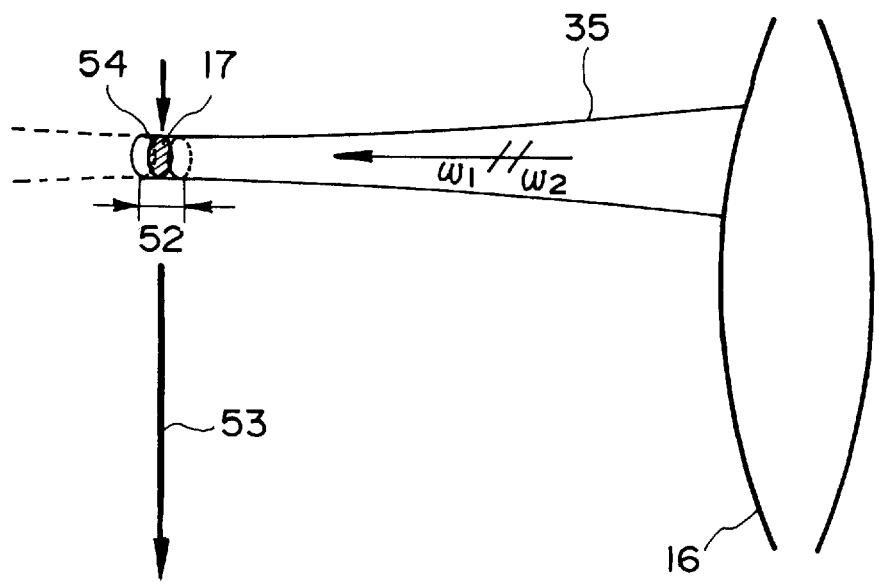
F I G. 2
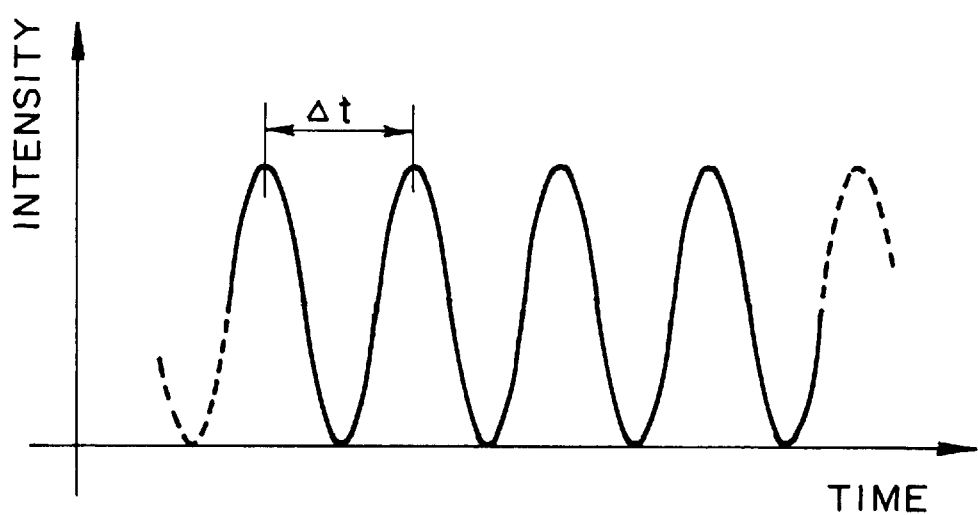
F I G. 3

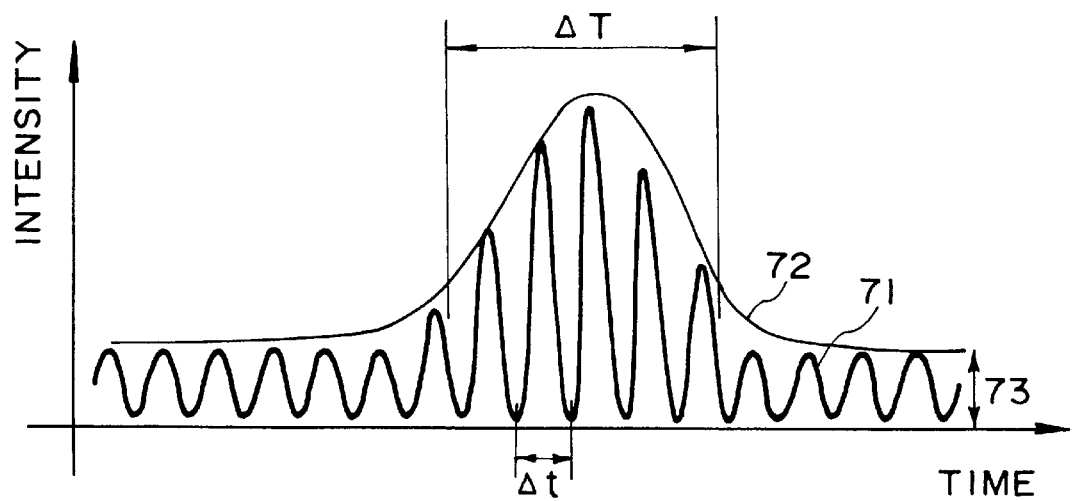
F I G. 5
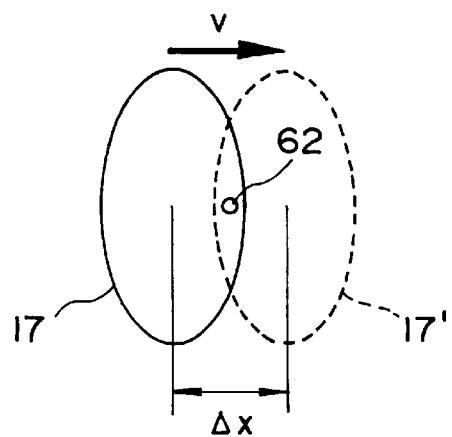
F I G. 6

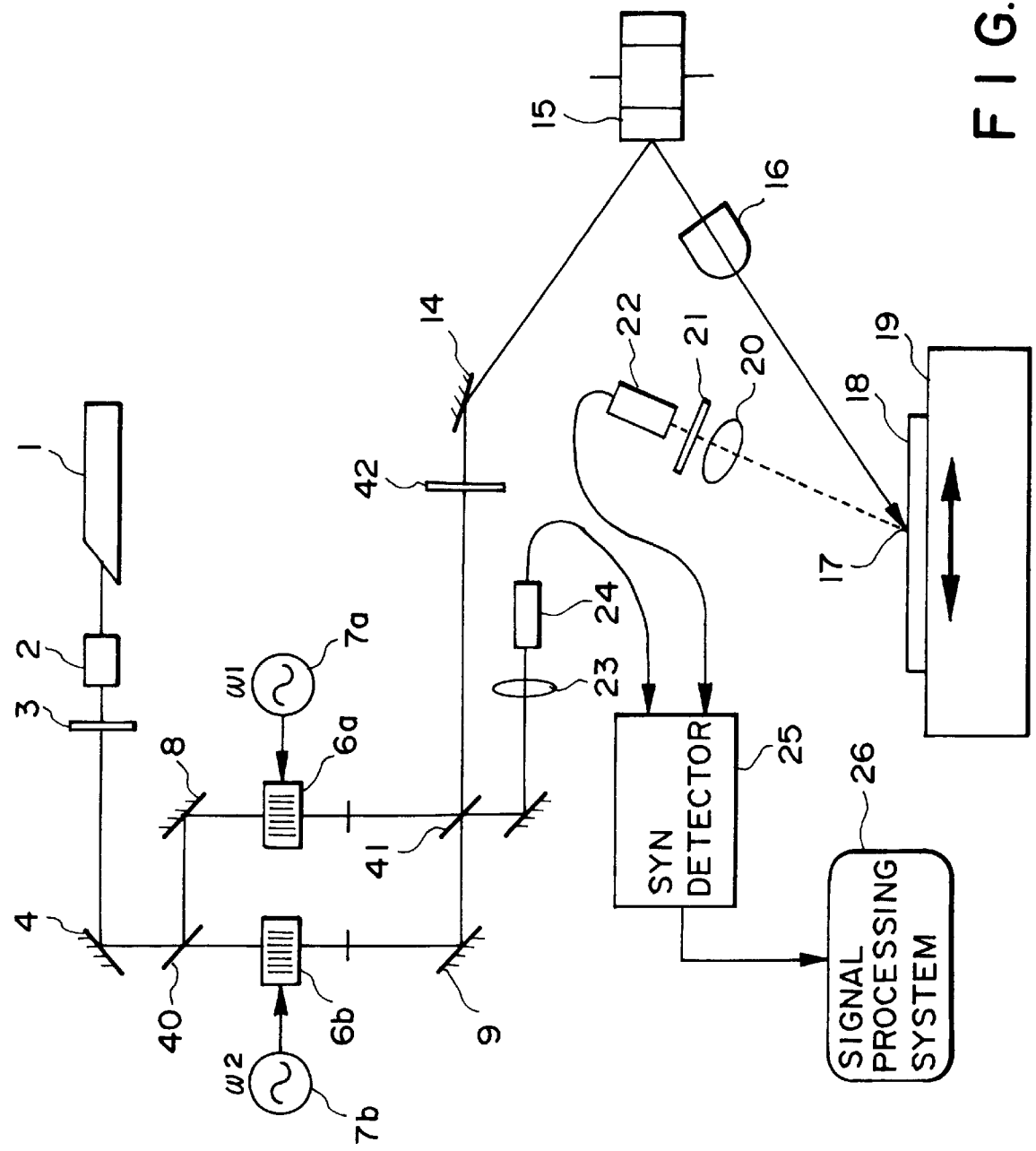
F I G. 7

OPTICAL INSPECTION METHOD AND APPARATUS INCLUDING INTENSITY MODULATION OF A LIGHT BEAM AND DETECTION OF LIGHT SCATTERED AT AN INSPECTION POSITION

FIELD OF THE INVENTION AND RELATED ART

This invention relates to a method and an apparatus usable, as an example, in the manufacture of microdevices such as semiconductor devices, for inspecting the surface of an article. More particularly, the invention is concerned with a method and an apparatus for optically inspecting the presence/absence of minute particles or defects on the surface of an article. In another aspect, the invention is concerned with a method and an apparatus for manufacturing microdevices such as semiconductor devices by using such an inspection method.

For the manufacture of semiconductor devices such as ICs or liquid crystal displays, for example, a circuit pattern formed on an original (called a "reticle" or "photomask") is transferred to the surface of a workpiece or wafer having a resist coating by using a semiconductor printing apparatus (called an "exposure apparatus"). If in this transfer process there are minute particles (foreign particles) on the surface of the original, such particles are also transferred (printed) on the wafer. This causes a decreased yield of IC manufacture. Particularly, in a case where the same circuit pattern is printed on different zones of a wafer sequentially in accordance with the step-and-repeat method, only one particle on the original is printed on every zone of the wafer. This results in a possibility that all the chips produced from this wafer are defective, leading to a substantial decrease in the yield of IC manufacture.

In the IC manufacturing process, it is therefore desired to inspect the presence/absence of minute particles on an original, and many proposals have been made in this respect. FIG. 10 shows an example of an inspection apparatus. In this example, the presence/absence of any foreign particle is examined by detecting scattered light from the particle.

More particularly, in FIG. 10, a laser beam from a laser light source 151 is transformed into a laser beam best suited for inspection, by means of a polarizer 152, a filter 153, a collimating system 154 and so on. Mirror 155 directs the laser beam to a scanning optical system comprising a scanning mirror 157 and an f-θ lens 158. The scanning laser beam from the f-θ lens 158 is converged on the surface 160, to be inspected, of a reticle or the like having a circuit pattern formed thereon, and thus a scanning light spot 159 is formed thereon. A scanning stage system 166 serves to relatively move the scanning spot 159 and the surface 160 in a direction perpendicular to the direction of scan by the scanning spot 159, whereby a two-dimensional scan of the entire surface 160 is assured.

A detection system comprising a lens system 161, a polarizer 162, an aperture 163 and a photoelectric detector 164 is disposed to receive backward or sideward scattered light. As regards the disposition of this detection system, since there is scattered light from the circuit pattern or the like on the surface 160, which light has a particular direction of diffraction, the detection system has to be disposed off such a direction so as not to receive the unwanted diffraction light.

If in this structure there is no particle within the range of the scanning spot 159, no scattered light is detected by the photoelectric detector 164. If there is any particle, it produces scattered light isotropically and, therefore, the photoelectric detector 164 detects any scattered light. Thus, by processing an output signal of the detector in a signal processing system 165, the presence/absence of any foreign particle on the surface can be inspected.

SUMMARY OF THE INVENTION

However, in this type of inspection apparatus, if a very small particle of a size of, e.g., about 0.3 micron or less is to be detected, the produced scattered light has a very low intensity. It is therefore not easy to discriminate the particle-scattered light and any other stray light and thus to detect the particle-scattered light with good sensitivity.

It is accordingly an object of the present invention to provide a system that assures detection of even a small particle or defect, as described above, with a high signal-to-noise ratio.

It is another object of the present invention to provide a method of manufacture of a semiconductor device of a high degree of integration based on such an inspection system as discussed above.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 2 illustrates details of modulation in the neighborhood of a scanning light spot.

FIG. 3 illustrates the waveform of intensity modulation of the scanning light spot.

FIG. 5 is a graph of a scattered-light signal detected.

FIG. 6 is a schematic view for explaining the time interval for scanning a particle.

FIG. 7 is a schematic and diagrammatic view showing a second embodiment of the present invention.

DESCRIPTION OF THE PREFERRED EMBODIMENTS

Now, the invention will be described with reference to an inspecting system for inspecting an original (reticle or photomask) and a wafer which are used in the field of semiconductor technology, more particularly, for inspecting the presence/absence of any particle or defect on the surface to be examined. However, the applicability of the present invention is not limited to such as above, and the invention is widely applicable to other inspecting systems for inspecting a surface.

Embodiment 1

Figure 1:
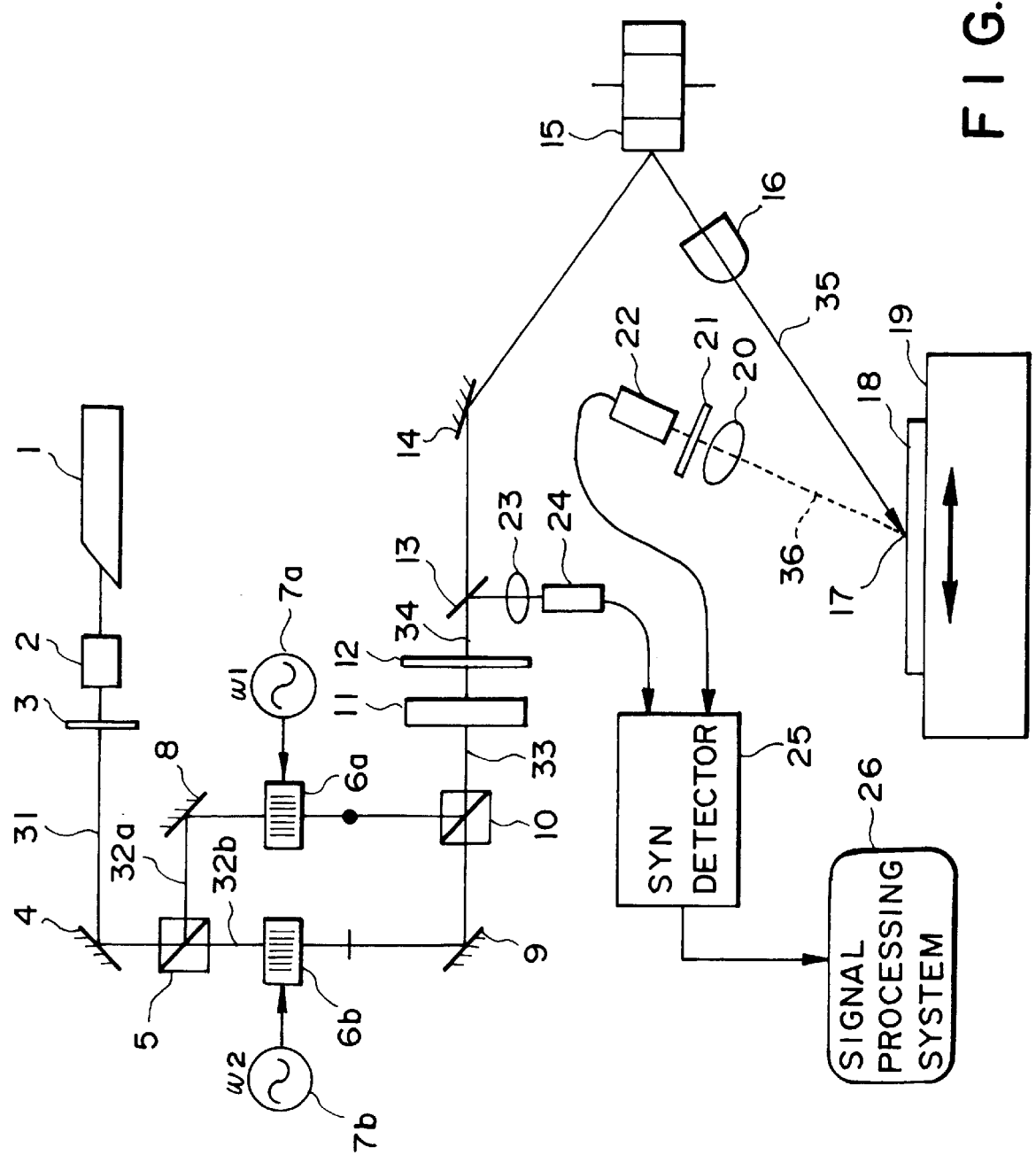
FIG. 1 is a schematic and diagrammatic view showing a first embodiment of the present invention.

FIG. 1 shows an inspecting system according to a first embodiment of the present invention. Denoted in the drawing at 1 is a laser light source for producing a rectilinearly polarized laser beam; at 2 is a collimating optical system for transforming the laser beam into a beam of an appropriate beam diameter; at 3 is a filtering system; at 4, 8, 9 and 14 are mirrors; at 5 is a wave divider (polarization beam splitter); at 6a and 6b are acousto-optic devices each for modulating laser light with an appropriate shift frequency; at 7a and 7b are drivers each for driving a corresponding one of the acousto-optic devices; at 10 is a wave combining element (polarization beam splitter); at 11 is a quarter waveplate for transforming rectilinearly polarized light into circularly polarized light; and at 12 is a polarizer. These elements cooperate with each other to provide a light source portion of the inspecting system.

Denoted at 13 is a half mirror; at 15 is a polygonal mirror; and at 16 is an f-θ lens system. The elements 15 and 16 cooperate with each other to provide a scanning optical system. Denoted at 18 is the surface of an original such as a reticle or photomask, which surface is the very one to be inspected. Denoted at 17 is a scanning light spot formed on the surface 18 to be examined. Denoted at 19 is a stage system for supporting and moving the original in predetermined directions (as denoted by an arrow in the drawing). Denoted at 20 and 23 are condensing lenses; at 22 and 24 are photoelectric detectors; at 25 is a synchronism detector; and at 26 is a signal processing system.

The laser beam from the laser light source 1 is transformed by the collimating optical system 2 into a laser beam of an appropriate beam diameter, and it enters the filtering system 3 having an ND (neutral density) filter and a polarizer, for example. By this filtering system, the laser beam is attenuated whereby a laser beam 31 of an appropriate intensity suited to the inspection is produced. The laser beam 31 is then divided by the wave divider 5 such as a polarization beam splitter, for example, into an S-polarized laser beam 32a and a P-polarized laser beam 32b. The S-polarized laser beam 32a is then modulated by the acousto-optic device 6a at a shift frequency w1, wherein the device 6a is driven by the driver 7a. Similarly, the P-polarized laser beam 32b is modulated by the acousto-optic device 6b at a shift frequency w2, wherein the device 6b is driven by the driver 7b. These modulated two rectilinearly polarized lights are combined into one laser beam 33 by means of the wave combining element 10 such as a polarization beam splitter. Thus, the laser beam 33 comprises two rectilinearly polarized components having orthogonally intersecting polarization directions and having a frequency difference $\Delta w$ (=|w1-w2|).

While in this embodiment two acousto-optic devices are used, only one acousto-optic device may be used to modulate one of the laser beams 32a and 32b at a shift frequency $\Delta w$. As a further alternative, a dual-frequency Zeeman laser may be used or an injection current to a semiconductor laser may be modulated. Each of these alternatives may provide light of the same property as the laser beam 33.

The laser beam 33 passes through the quarter waveplate 11 by which it is transformed from the rectilinearly polarized light into circularly polarized light. Thus, the resultant light comprises a combination of two circularly polarized laser components of frequencies w1 and w2, rotating in opposite directions. By subsequently passing the polarizer 12 having its axis of polarization set in a predetermined direction (the direction of S-polarization, in this embodiment), the directions of polarization of these laser beam components are registered with each other, whereby a rectilinearly polarized laser beam 34 which comprises the combination of components of the frequencies w1 and w2, having a registered direction of polarization, is produced.

Subsequently, the laser beam 34 is divided by the half mirror 13. One laser beam as reflected by the half mirror is collected by the condensing lens 23 onto the photoelectric conversion surface of the photoelectric detector 24. Since the collected laser causes, at the position collected, a light beating due to optical heterodyne interference, the photoelectric detector 24 detects a beat signal 24a of a frequency $\Delta w$. This signal is subsequently used in the synchronism detector 25 as a reference signal for the synchronism detection.

On the other hand, the other laser beam passing through the half mirror 13 enters the scanning optical system comprising the polygonal mirror 15 and the f-θ lens system 16. The laser beam is deflected by this scanning optical system, whereby a laser beam denoted at 35 is provided. This laser beam 35 is converged on the surface 18 to be examined, to form a scanning light spot 17. With the rotation of the polygonal mirror 15, the scanning light spot displaces along a direction perpendicular to the sheet of the drawing, to thereby optically scan the surface 18 to be examined. The stage 19 may be moved simultaneously with this optical scanning, in a direction perpendicular to the direction of scan, such that the surface 18 may be scanned two-dimensionally.

The action in the neighborhood of the scanning light spot 17 will now be explained in greater detail, with reference to FIG. 2. In the drawing, denoted at 52 is the depth of focus as determined by the f-θ lens system 16; at 53 is the direction of scan; and at 54 is the interference region in which the intensity modulation occurs. The laser beam 35 emanating from the f-θ lens system 16 comprises the combination of two rectilinearly polarized laser components having different frequencies w1 and w2 and having a registered direction of polarization. This laser 35 is converged on the surface to be examined, to provide the scanning light spot 17. At the position where the scanning light spot is formed, the rectilinearly polarized lasers interfere with each other to cause what can be called "optical heterodyne interference". This optical heterodyne interference is caused within the region 54, and this region 54 is dependent upon the depth of focus (denoted at 52) of the f-θ lens system which is of an order of a few tens of microns in this embodiment. In this interference region 54, the optical heterodyne interference occurs under "one color condition" and, as a consequence, the intensity of the scanning light spot 17 is modulated at a beat frequency $\Delta w$. Thus, the resultant is such as shown in FIG. 3 wherein darkness and brightness are repeated like a sine wave (period $\Delta t=1/\Delta w$) through the light spot area on the surface to be inspected. Namely, it can be said that the scanning light spot 17 is intensity modulated substantially with a frequency $\Delta w$.

As described, the region in which the laser 35 is modulated through optical heterodyne interference is small (i.e., only in the small region 54), and substantially no intensity modulation occurs in the space between the region 54 and the laser light source 1. As a consequence, even if there is produced any stray light (from any optical component) in this space, such stray light is not at all intensity modulated in this space and thus it does not have a frequency component $\Delta w$. It is therefore possible to exclude noises due to such stray light, through the subsequent synchronism detection.

Figure 4:
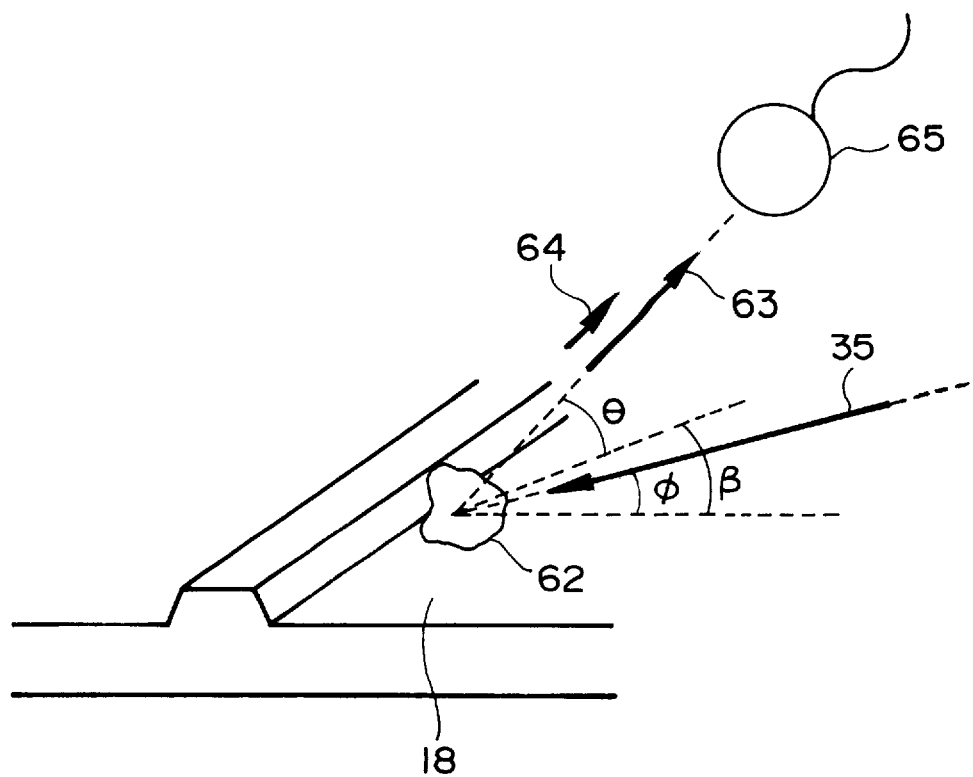
FIG. 4 is a schematic and enlarged view of a portion about the scanning light spot.

FIG. 4 is an enlarged view for explaining the detection of a particle or defect on the surface to be examined. Denoted at 62 is the particle to be detected. Denoted at 63 is light scattered by the particle; at 64 is light scattered by an edge of a circuit pattern, for example, on the surface being examined; and denoted at 65 is the detection system. The laser light 35 from the scanning optical system is incident on the surface 18 being examined, at an angle φ, and it is converged thereon to form a scanning light spot. On the other hand, the direction of detection of the detection system 65 is set to be in the backward and sideward scatter directions (of angles β and θ as illustrated with respect to the direction of incidence). In determination of the direction of detection, such an angle with which only a small scattered light comes from anything other than the particle 62 (e.g., scattered light from the circuit pattern), is selected. Also, while the laser light 35 comprises rectilinearly polarized light, the orientation of the polarizer 12 (FIG. 1) is so determined that the direction of polarization of the laser light 35 is best suited to the inspection of a particle or defect.

Referring back to FIG. 1, if scattered light is produced from the scanning light spot, by a particle or defect on the surface being examined, such scattered light has an intensity modulated in synchronism with the intensity modulation frequency Δw of the scanning light spot. Such intensity-modulated scattered light 36 is received by the condensing lens 20 which is disposed along the optimum detection direction as described, and, through the filtering system 21 comprising a polarizer, for example, it is detected by the photoelectric detector 22. The filtering system 21 serves to block the scattered light from the circuit pattern (as it has a particular plane of polarization) and to selectively and partially transmit the scattered light from a particle or defect (as it has various polarization planes due to polarization cancellation). Thus, the filtering system is contributable to reducing the effect of the circuit pattern and to enhancing the signal-to-noise ratio. The detection signal corresponding to the scattered light as detected by the photoelectric detector 22 is applied to the synchronism detector 25. As has been described hereinbefore, a reference signal of a frequency Δw from the photoelectric detector 24 also is applied to this synchronism detector 25. Thus, while taking synchronism with this reference signal, only that component of the detection signal of the scattered light that has a frequency Δw is detected. Then, on the basis of an output signal from the synchronism detector 25, the discrimination of the presence/absence of any particle or defect is executed in the signal processing system 26. Also, data memorization or data display processing is executed in this signal processing system.

The synchronism detector 25 may comprise a lock-in amplifier, for example. It serves to extract, out of the detection signal corresponding to the detected scattered light, a signal of a frequency component Δw, in synchronism with the reference signal. As a possible alternative, the synchronism detector 25 may comprise a combination of a detecting circuit and a frequency filter having a high frequency selectivity. On that occasion, the application of a reference signal is not necessary.

FIG. 5 shows an example of a scattered-light detection signal obtainable from the photoelectric detector 22. Denoted at 71 is a curve which depicts the signal intensity. Denoted at 71 is an envelope, and denoted at 73 is a noise level. Since the scanning light spot 17 has been intensity modulated at a frequency Δw, the intensity of the scattered light is also modulated at Δw (=1/Δt) correspondingly, such as the curve 71.

Through the synchronism detector 25 and the signal processing system 26, a signal such as depicted by the envelope 72 is detected and, while taking into account the noise level 73, the discrimination of any particle or defect is carried out. Here, the time period ΔT in which scattered light occurs due to a particle or defect is determined by the size of the scanning light spot 17 and the scan speed for scanning the surface 18 with this light spot 17, as depicted in FIG. 6. More specifically, as illustrated in FIG. 6, the time interval of displacement of the scanning light spot, moving at a speed V, from the position where one end of the scanning light spot 17 reaches a particle 62, to the position as depicted by a broken line 17', does correspond to the signal time period ΔT.

It is to be noted here that the intensity modulation period Δt should be smaller than the time period ΔT in which scattered light is produced from a particle or defect. For example, it is preferable to determine the scan speed V and the frequency Δw so as to satisfy a relation Δt<ΔT/5. Namely, the laser shift frequency and the number of revolutions of the polygonal mirror may preferably be selected so as to satisfy:

$$\Delta w > w_{scan} \times 5$$

wherein $w_{scan}$ is the optical scan frequency.

The above-described embodiment provides the following advantageous effects:

(1) Since any stray light from a portion other than the scanning light spot is not intensity modulated, it is possible to reduce noise remarkably through the synchronism detection.

(2) Synchronism detection a the modulated signal effectively reduces adverse effects of a 1/f noise, such as a shot noise of a photoelectric detector, upon a detected signal. Thus, it is possible to detect even a weak scattered light from a particle, at a high signal-to-noise ratio.

(3) Intensity modulation of the scanning light based on optical heterodyne interference easily assures attainment of a high modulation frequency (e.g., a few tens of megahertz). Thus, it is possible to meet a high scanning speed. This means that the surface can be inspected quickly.

Embodiment 2

FIG. 7 shows a second embodiment of the present invention. Like numerals as those in FIG. 1 are assigned to corresponding elements. This embodiment is based on the same basic principle as that of the embodiment of FIG. 1. However, the structure of the light source portion is modified. Denoted at 40 is a half mirror (wave divider); at 41 is another half mirror (wave combining element); and at 42 is a filtering system provided for intensity setting. In this embodiment, since the half mirror 40 is used to divide the laser (for subsequent modulation to the divided lasers at different shift frequencies), the divided lasers have registered polarization directions. The modulated lasers are combined by the half mirror 41. Like the laser 34 in FIG. 1, the thus combined laser comprises a combination of rectilinearly polarized components of frequencies w1 and w2, having registered polarization directions. One of the laser beams divided by the half mirror 41 is detected by the photoelectric detector 24 as reference light, while the other laser beam goes through the filtering system 42 to the scanning optical system. Since this embodiment uses a half mirror, there is no necessity of using a quarter waveplate or a polarizer as in the preceding embodiment.

In both of the first and second embodiments described, the laser light impinging on the surface to be examined is intensity modulated on the basis of optical heterodyne interference and this easily assures attainment of a high modulation frequency (e.g., a few tens of megahertz). However, for a simpler structure, a modulating element such as an acousto-optic element or a chopper may be disposed on the light path to effect intensity modulation. Alternatively, the light source itself may be controlled to modulate the intensity of light to be emitted.

Embodiment 3

Figure 8:
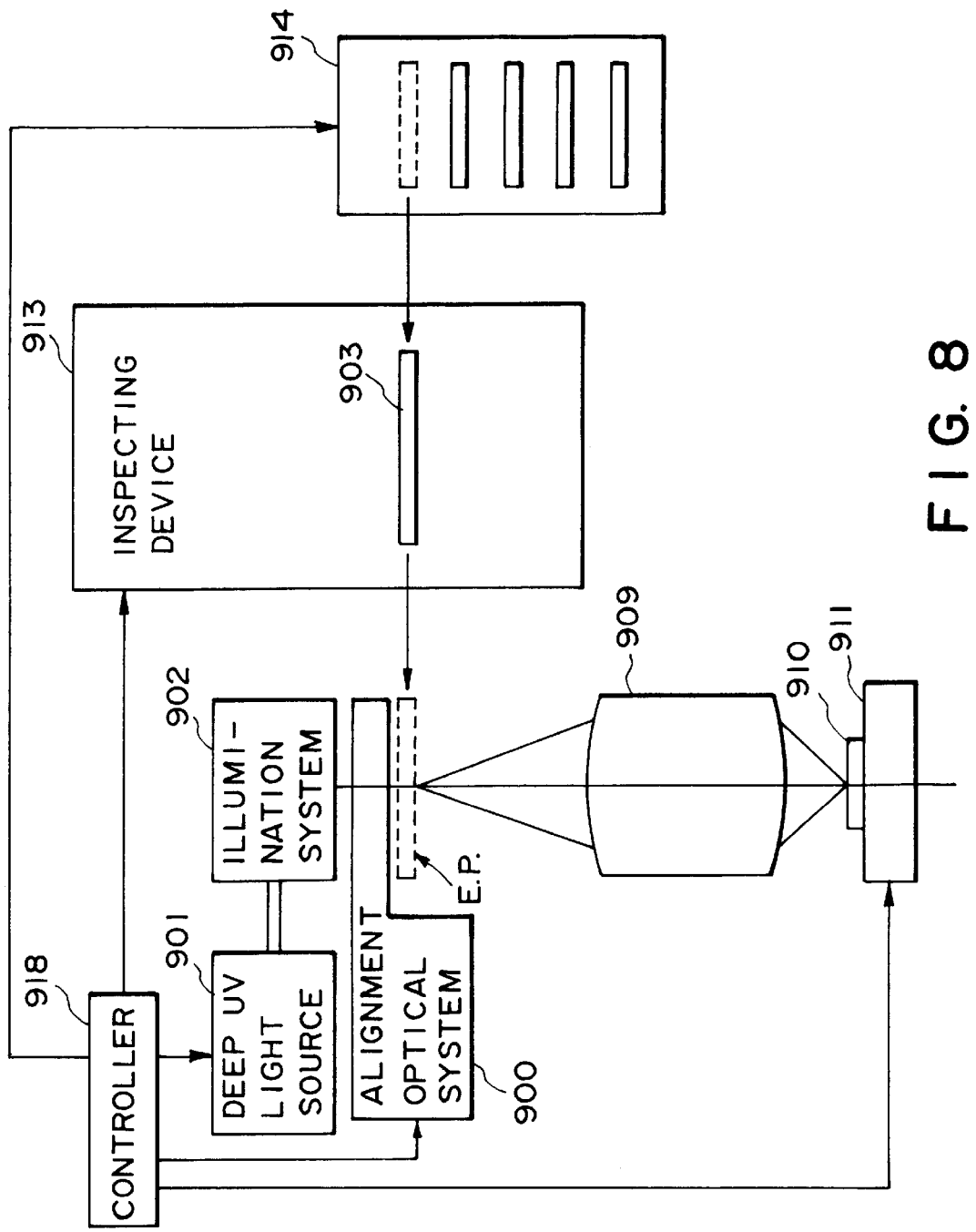
FIG. 8 is a schematic and diagrammatic view of a semiconductor device manufacturing system according to the present invention.

FIG. 8 shows an embodiment of a semiconductor device manufacturing system for printing a circuit pattern of an original such as a reticle or photomask upon a silicon wafer. Generally stating, this system comprises an exposure apparatus, an original storing device, an original inspecting device and a controller, all being placed in a clean room.

Denoted at 901 is a deep ultraviolet light source such as an excimer laser, for example, and denoted at 902 is an illumination system unit for illuminating an original, held at an exposure position (E.P.), simultaneously (whole surface illumination) from above and with a predetermined numerical aperture (NA). Denoted at 909 is an ultra-high-resolution lens system (or mirror system) for transferring the circuit pattern formed on the original onto a silicon wafer 910. Upon printing, the wafer is shifted one-shot by one-shot with stepwise motion of a movable stage 911 so that repeated exposures are made thereto. Denoted at 900 is an alignment optical system for aligning the original and the wafer prior to the exposure operation. It includes at least one original observing microscope system. These elements constitute the exposure apparatus.

On the other hand, denoted at 914 is the original storing device for accommodating therein a plurality of originals. Denoted at 913 is the original inspecting device which has the structure according to any one of the preceding embodiments. The inspecting device 913 serves to execute particle inspection to a selected one of the originals, taken out of the storing device 914, before it is placed at the exposure station EP. The principle and manner of particle inspection is the same as that of the corresponding embodiment. Controller 918 serves to control the sequence of the whole system and, as an example, it controls the operation of the storing device 914 and the inspecting device 913 as well as the alignment and exposure operation and wafer stepwise operation which are basic operations of the exposure apparatus.

A semiconductor device manufacturing process using the system of the present embodiment will now be explained. First, an original to be used is taken out of the original storing device 914 and it is placed in the inspecting device 913. Then, particle inspection to this original is executed through the inspecting device. If, as a result of inspection, it is discriminated that no particle is present on the original, the original is then placed at the exposure station EP in the exposure apparatus. Subsequently, a silicon wafer 910 which is an article to be exposed is placed on the movable stage 911. Then, while moving the movable stage 911 stepwise and shifting the wafer one-shot by one-shot in accordance with the step-and-repeat method, the pattern of the original is projected in a reduced scale on different zones of the silicon wafer to expose them. After the exposure process to one wafer is completed, this wafer is off-loaded and a new silicon wafer is loaded, and step-and-repeat exposures of it to the pattern of the original are repeated in the same manner.

The "exposed" wafer whose exposure process is completed, is subjected to a developing process, an etching process and so on through respective devices provided separately from the illustrated system. After this, it is subjected to assembling processes such as dicing, wire bonding, packaging and so on, whereby semiconductor devices are finished.

Embodiment 4

Figure 9:
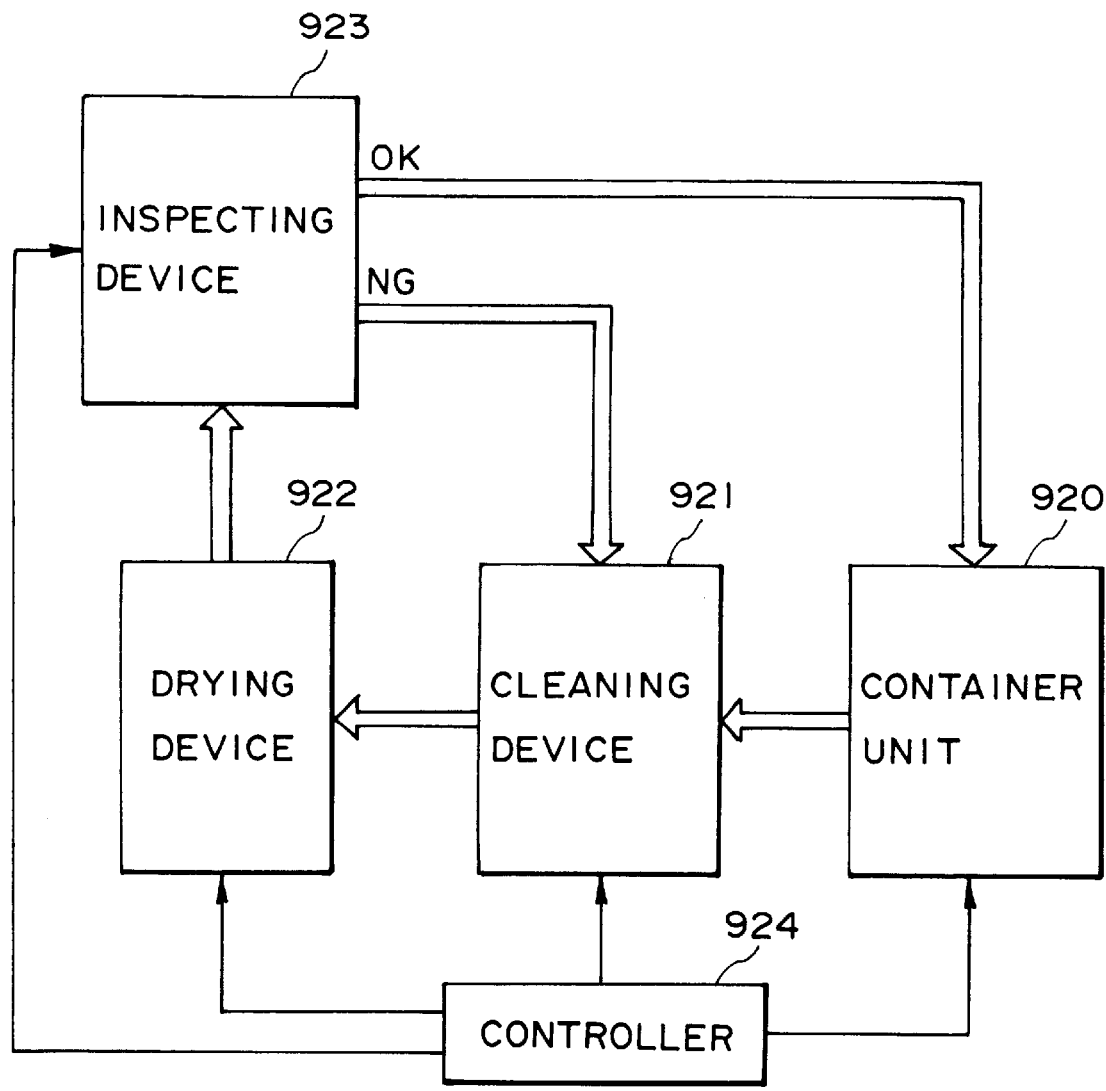
FIG. 9 is a schematic and diagrammatic view of an original cleaning and inspecting system according to the present invention.
Figure 10:
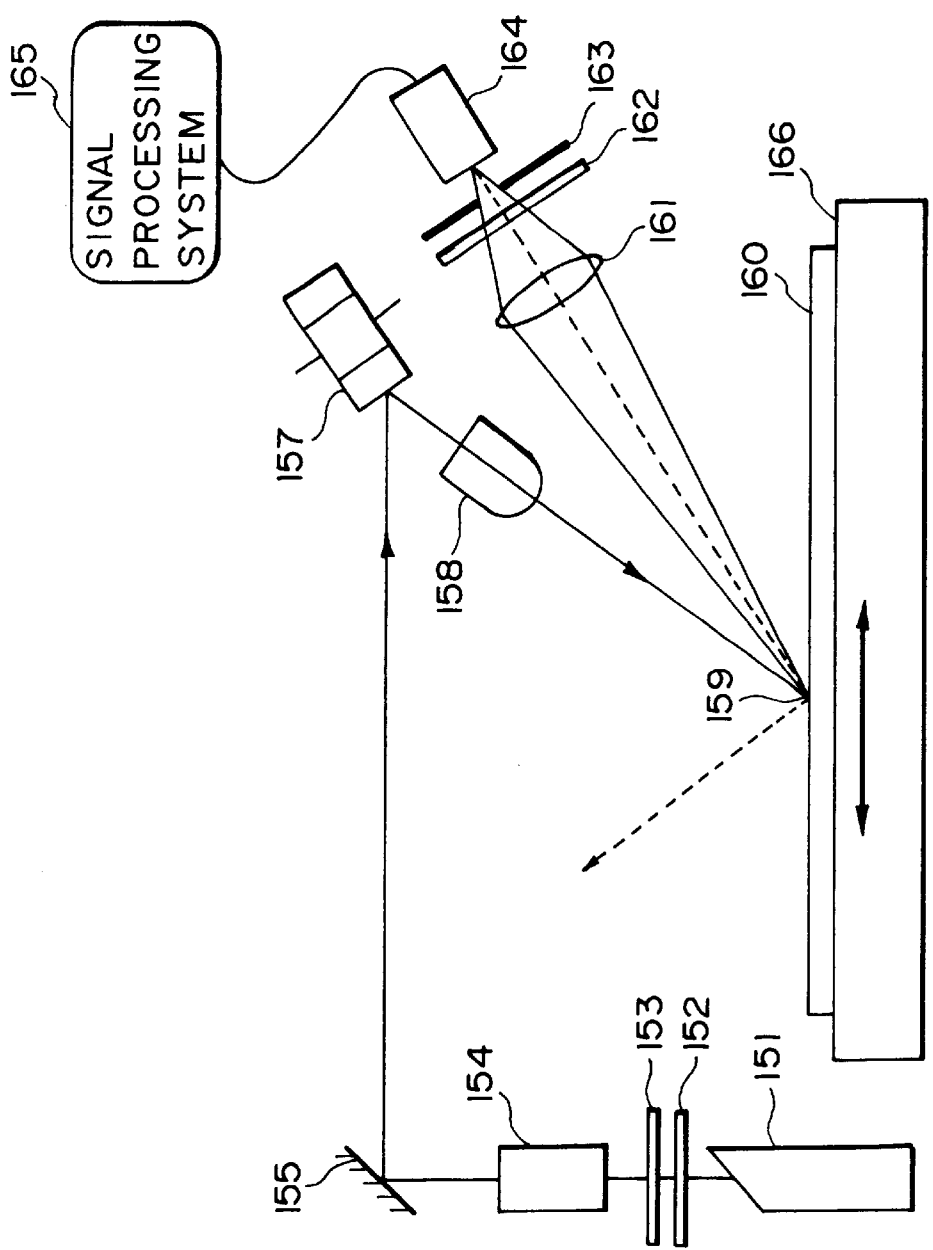
FIG. 10 is a schematic view of a known type of an inspecting apparatus.

FIG. 9 shows an embodiment of an original cleaning and inspecting system for the manufacture of semiconductor devices. Generally stating, the system comprises an original storing device, a cleaning device, a drying device, an inspecting device and a controller, all being placed in a clean room.

The operation will be explained. First, an original to be cleaned is taken out of the original storing device 920 and it is moved into the cleaning device 921. After the cleaning in the cleaning device 921, the cleaned original is moved into the drying device 922 and is dried. After it is dried, it is moved into the inspecting device 923. In this inspecting device, any foreign particle on this original is inspected in accordance with the method of any one of the embodiments described hereinbefore. If as a result of inspection no particle is detected, the original is moved back into the storing device 920. If a particle is detected, the original is moved back to the cleaning device 921 and, after repetition of the cleaning and drying operations it is inspected again. This is repeated until particles are totally removed, and a completely cleaned original is moved back into the storing device 920.

Subsequently, such a cleaned original is placed in an exposure apparatus and the printing of a circuit pattern of the original on a silicon wafer is executed, for the manufacture of semiconductor devices.

While the invention has been described with reference to the structures disclosed herein, it is not confined to the details set forth and this application is intended to cover such modifications or changes as may come within the purposes of the improvements or the scope of the following claims.

What is claimed is:

1. An optical inspection device, comprising:
   an optical system for modulating an intensity distribution of light to be projected to an inspection position where the inspection is to be carried out, said optical system comprising (i) light source means for generating first and second light beams being superposed one upon another and having different frequencies w1 and w2, respectively, said light source means including one of an acousto-optic device and a dual-frequency laser for emitting a dual-frequency laser beam having different frequency components corresponding to those of the two light beams, respectively, and (ii) a lens for substantially collecting the superposed first and second light beams at an inspection position, said lens projecting the first and second light beams onto the inspection position along the same direction, wherein, as a result of the collection of the first and second light beams, heterodyne interference at a modulation frequency |w1−w2| is produced in the neighborhood of the inspection position; and
   detecting means comprising a synchronism detector, for detecting scattered light, being scattered at the inspection position, having the modulation frequency |w1−w2|.

2. A device according to claim 1, further comprising a laser source for providing the light beam.

3. A device according to claim 1, further comprising scanning means for scanning a surface, to be examined, with the light beam.

4. An optical inspection method, comprising the steps of:
   modulating an intensity distribution of light to be projected to an inspection position where the inspection is to be carried out, said modulating step comprising (1)

generating first and second light beams being superposed upon one another and having different frequencies w1 and w2, respectively, by using one of an acousto-optic device and a dual-frequency laser for emitting a dual-frequency laser beam having different frequency components corresponding to those of the two light beams, respectively, and (ii) substantially collecting the first and second light beams, being superposed one upon another, at an inspection position by using a lens, projecting the first and second light beams, by the lens, onto the inspection position along the same direction, and producing, as a result of the collection of the first and second light beams, heterodyne interference at a modulation frequency |w1–w2|, in the neighborhood of the inspection position; and detecting, by use of a synchronism detector, scattered light being scattered at the inspection position, having the modulation frequency |w1–w2|.

5. An exposure system, comprising:

an optical inspecting device for inspecting an original having a pattern to be exposed, said inspecting device comprising (a) an optical system for modulating an intensity distribution of light to be projected to an inspection position where the inspection is to be carried out, said optical system comprising (i) light source means for generating first and second light beams being superposed one upon another and having different frequencies w1 and w2, respectively, said light source means including one of an acousto-optic device and a dual-frequency laser for emitting a dual-frequency laser beam having different frequency components corresponding to those of the two light beams, respectively, (b) a lens for substantially collecting the superposed first and second light beams at an inspection position, said lens projecting the first and second light beams onto the inspection position along the same direction, wherein, as a result of the collection of the first and second light beams, heterodyne interference at a modulation frequency |w1–w2| is produced in the neighborhood of the inspection position, and (c) detecting means, comprising a synchronism detector, for detecting scattered light, being scattered at the inspection position, having the modulation frequency |w1–w2|; and an exposure device for exposing the pattern of the original to print the pattern on a substrate.

6. An original cleaning and inspecting system, comprising:

a cleaning device for cleaning an original; and an optical inspecting device for inspecting the original cleaned by said cleaning device, said inspecting device comprising (a) an optical system for modulating an intensity distribution of light to be projected to an inspection position where the inspection is to be carried out, said optical system comprising (i) light source means for generating first and second light beams being superposed one upon another and having different frequencies w1 and w2, respectively, said light source means including one of an acousto-optic device and a dual-frequency laser for emitting a dual-frequency laser beam having different frequency components corresponding to those of the two light beams, respectively, and (ii) a lens for substantially collecting the superposed first and second light beams at an inspection position, said lens projecting the first and second light beams onto the inspection position along the same direction, wherein, as a result of the collection of the first and second light beams, heterodyne interference at a modulation frequency |w1–w2| is produced in the neighborhood of the inspection position, and (b) detecting means, comprising a synchronism detector, for detecting scattered light, being scattered at the inspection position, having the modulation frequency |w1–w2|.

7. A semiconductor device manufacturing method, comprising the steps of:

inspecting an original having a circuit pattern, said inspecting step comprising (a) modulating an intensity distribution of light to be projected to an inspection position on the original where the inspection is to be carried out, said modulating step comprising (1) generating first and second light beams being superposed one upon another and having different frequencies w1 and w2, respectively, by using one of an acousto-optic device and a dual-frequency laser for emitting a dual-frequency laser beam having different frequency components corresponding to those of the two light beams, respectively, and (2) substantially collecting the first and second light beams, being superposed one upon another, at an inspection position by using a lens, projecting the first and second light beams, by the lens, onto the inspection position along the same direction, and producing, as a result of the collection of the first and second light beams, heterodyne interference at a modulation frequency |w1–w2|, in the neighborhood of the inspection position and (b) detecting, by use of a synchronism detector, scattered light being scattered at the inspection position, having the modulation frequency |w1–w2|; and exposing the circuit pattern of the inspected original to print the pattern on a wafer.

8. A semiconductor device manufactured by a method which comprises the steps of:

inspecting an original having a circuit pattern, said inspecting step comprising (a) modulating an intensity distribution of light to be projected to an inspection position on the original where the inspection is to be carried out, said modulating step comprising (1) generating first and second light beams being superposed upon one another and having different frequencies w1 and w2, respectively, by using one of an acousto-optic device and a dual-frequency laser for emitting a dual-frequency laser beam having different frequency components corresponding to those of the two light beams, respectively, and (2) substantially collecting the first and second light beams, being superposed one upon another, at an inspection position by using a lens, projecting the first and second light beams, by the lens, onto the inspection position along the same direction, and producing, as a result of the collection of the first and second light beams, heterodyne interference at a modulation frequency |w1–w2|, in the neighborhood of the inspection position and (b) detecting, by use of a synchronism detector, scattered light being scattered at the inspection position, having the modulation frequency |w1–w2|; and exposing the circuit pattern of the inspected original to print the pattern on a wafer.

\* \* \* \* \*